United States Patent
Wyrzykiewicz et al.

(10) Patent No.: US 6,900,308 B2
(45) Date of Patent: May 31, 2005

(54) α-MODIFIED NUCLEOSIDE TRIPHOSPHATES

(75) Inventors: Tadeusz Wyrzykiewicz, Carlsbad, CA (US); Phillip Dan Cook, Fallbrook, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 7 days.

(21) Appl. No.: 10/195,980

(22) Filed: Jul. 16, 2002

(65) Prior Publication Data

US 2003/0129615 A1 Jul. 10, 2003

Related U.S. Application Data

(60) Provisional application No. 60/305,652, filed on Jul. 16, 2001.

(51) Int. Cl.$^7$ ............................................. C07H 19/04
(52) U.S. Cl. .................................... 536/26.2; 536/26.1
(58) Field of Search ............................. 536/26.1, 26.2; 435/6

(56) References Cited

U.S. PATENT DOCUMENTS

| | | | |
|---|---|---|---|
| 5,359,052 A | 10/1994 | Stee et al. | |
| 5,861,501 A | 1/1999 | Benseler et al. | |

FOREIGN PATENT DOCUMENTS

| | | | | |
|---|---|---|---|---|
| WO | WO 01/14401 | * | 3/2001 | ........... C07H/19/10 |

OTHER PUBLICATIONS

Shaw et al, Chemical Communication, 2000, 2115–2116, Published on the Web Oct. 11, 2000.*
Shaw et al J.Org. Chem. 1998, 63, 5769–5773.*
Schneider et al, Nucleosides, Nucleotides & Nucleic Acids, 2001, 20(4–7), 297–306, published on–line Mar. 31, 2001.*
Meyer, etal "Structural basis for activation of alpha–boranophosphatnucleotide analogues targeting drug–resistant reverse transcriptase", The EMBO Journal, 2000, 19(14), 3520–2529.*
Okruzsek et al "The Synthesis of Nucleoside 5'–O–(1, 1–Dithiotriphosphates)", J. Med. Chem. 1994, 37, 3850–3854.*
Mori, K., et al., "Phosphoroselenoate oligodeoxynucleotides: synthesis, physico–chemical characterization, antisense inhibitory properties and anti–HIV activity," *Nucleic Acids Res.,* Oct. 1989, 17(20), 8207–8219.
Copy of PCT International Search Report dated Dec. 13, 2002 (PCT/US02/22444).
Brownlee, G.G., et al., "Solid phase synthesis of 5'–diphosphorylated oligoribonucleotides and their conversion to capped m$_7$ Gppp–oligoribonucleotides for use as primers for influenza A virus RNA polymerase in vitro," *Nucleic Acid Research,* 1995, 23(14), 2641–2647.
Burgess, K., et al., "Synthesis of nucleoside triphosphates," *Chem. Rev.,* 2000, 100, 2047–2059.
Eckstein, F., "Nucleoside Phosphorothioates," *Ann. Rev. Biochem.,* 1985, 54, 367–402.
Gaur, R.K., et al., "Novel solid phase synthesis of 2'–o–methylribonucleoside 5'–triphosphates and their α–THIO analogues," *Tetrahedron Letters.,* 1992, 33, 3301–3304.
He, K., et al., "Synthesis and separation of diastereomers of ribonucleoside 5'–(α–P–Borano)triphosphates," *J. Org. Chem.,* 1998, 63, 5769–5773.
Krzyzanowska, B.K., et al., "A convenient synthesis of 2'–deoxyribonucleoside 5'–(α–P–Borano)triphosphates," *Tetrahedron,* 1998, 54, 5119–5128.
Ludwig, J., "A new route to nucleoside 5'–triphosphates," *Acta Biochim. Biophys. Acid. Sci. Hung.,* 1981, 16(3–4), 131–133.
Ludwig, J. et al., "Rapid and Efficient Synthesis of Nucleoside 5'–O–(1–Thiotriphosphates), 5'–Triphosphates and 2', 3'–Cyclophosphorothioates Using 2'Chloro–4H–1,3, 2–benzodioxaphosphorin–4–one," *J. Org. Chem.,* 1989, 54,631–635.
Meyer, P., et al., "Structural basis for activation of α–boranophosphate nucleotide analogues targeting drug–resistant reverse transcriptase," *The EMBO Journal,* 2000, 19(14), 3520–3529.
Nyilas, A., "Synthesis of pppA2'p5'A2'p5'A2'p5'A γ–amidates by one pot procedure from A2'p5'A2'p5'A," *Tetrahedron Letters,* 1997, 38(14), 2517–2518.
Schneider, B., et al., "Activation of anti–reverse transcriptase nucleotide analogs by nucleoside diphosphate kinase: improvement by α–boranophosphate substitution," *Nucleosides, Nucleotides & Nucleic Acids,* 2001, 20(4–7), 297–306.
Simoncsits, A., et al., "A new type of nucleoside 5'–triphosphate analog P$_1$–(nucleoside 5'–) P$_1$–amino–triphosphates," *Tetrahedron Letters,* 1976, 44, 3995–3998.
Tomasz, J., et al., "Chemical synthesis of 5'pyrophosphate and triphosphate derivatives of 3'–5' ApA, ApG, GpA and GpG study of the effect of 5'–phosphate groups on the confirmation of 3'–5–' Gpg," *Nucleic Acids Research,* Aug. 1978, 5(8), 2945–2957.
Stawinski, J., et al., "Nucleoside H–phosphonates. 14. Synthesis of nucleoside phosphoroselenoates and phosphorothioselenoates via stereospecific selenization of the corresponding H–phosphonate and H–Phosphonothioate diesters with the aid of new selenium–transfer reagent, 3H–1, 2–benzothiaselenol–3–one," *J. Org. Chem.,* 1994, 59, 130–136.
Victorova, et al., "Formation of phosphonester bonds catalyzed by DNA polymerase," *Nucleic Acids Research,* 1992, 20(4), 783–789.

* cited by examiner

*Primary Examiner*—James O. Wilson
*Assistant Examiner*—Ganapathy Krishnan
(74) *Attorney, Agent, or Firm*—Woodcock Washburn LLP

(57) ABSTRACT

The present invention is directed to α-modified nucleoside triphosphates and methods for their preparation. The present invention also provides for methods of inhibiting RNA and viral replication in cells, as well as methods for treating viral infections.

14 Claims, 3 Drawing Sheets

α-MODIFIED NUCLEOSIDE TRIPHOSPHATES

CROSS REFERENCE TO RELATED APPLICATIONS

This application claims the benefit of U.S. Provisional Application No. 60/305,652, filed Jul. 16, 2001, which is incorporated herein by reference in its entirety.

FIELD OF INVENTION

The present invention relates to modified triphosphate nucleoside compounds and methods for their preparation. The present methods provide modified nucleoside triphosphate compounds having at least one modification at the α-position of the triphosphate.

BACKGROUND OF THE INVENTION

Nucleoside triphosphate compounds can be polymerized to provide ribonucleic acid (RNA) and deoxyribonucleic acid (DNA). Apart from the traditional role in normal cells, these nucleic acids form the genetic materials of a variety of pathogenic viruses such as HIV, herpes, measles, mumps and many others. Many nucleoside triphosphates are not particularly robust, and they also tend to be difficult to synthesize. Many methods involve difficult combinations of charged ionic reagents with more lypophilic substrates, such as combinations of pyrophosphates and protected nucleosides. According to Burgess, et al., *Chem. Rev.,* 2000, 100, 2047–2059, many current methods are unable to provide high yields or allow a diverse set of nucleoside triphosphates to be made via a combinatorial or high throughput parallel synthesis.

The three phosphate moieties of nucleoside triphosphates are designated α, β, γ, where the α-phosphate is positioned closest to the sugar moiety. α-Phosphate substitutions in nucleoside triphosphate analogues have proven useful in elucidation of enzymatic functions and mechanisms. For example, exchange of one of the α-phosphate oxygens for sulfur, borane or methyl has allowed investigations of the stereochemical course of certain enzymatic reactions. (See, e.g., Eckstein, et al.,*Ann. Rev. Biochem.,* 1985, 54, 367–402; Kaizhang, et al., *J. Org. Chem.,* 1998, 63, 5769–5773; and Victorova, et al., *Nucleic Acids Research,* 1992, 20, 783–789).

Further, nucleoside triphosphates have important therapeutic and diagnostic applications. These molecules have found important roles, for example, in inhibition of viral replication as is characteristic of AIDS chemotherapy (see, e.g., Meyer, et al., *The EMBO Journal,* 2000, 19, 3520 and Schneider, et al., *Nucleosides, Nucleotides & Nucleic Acids,* 2001, 20, 297). Nucleoside triphosphates and derivatives thereof have also been found to have promising anticancer, hypolipidemic, antiinflammatory, and antiosteoporotic activities.

Accordingly, preparation of nucleosides and their derivatives has been studied for many years. For example, Simoncsits, et al., *Tetrahedron Letters,* 1976, 44, 3995–3998, report the synthesis of 5'-α-amino-triphosphates based on the selective replacement of one of the two amide groups of 5'-phosphorodiamidates. Ludwig, *Acta Biochim. Biophys. Acad. Sci. Hung.,* 1981, 16, 131–133, reports a route to nucleoside 5'-triphosphates. α-P modified nucleoside triphosphate analogs are reported in International Publication Number WO 01/14401. Ludwig, et al., *J. Org. Chem.,* 1989, 54, 631–635, reports a method of making nucleoside 5'-triphosphates and α-thio analogues that requires the protection of the ribose 2' and 3' hydroxyl groups and produces byproducts that are difficult to remove. Gaur, et al., *Tetrahedron Letters,* 1992, 33, 3301–3304, disclose a method of making nucleoside 5'-triphosphates and α-thio analogues using a functionalized solid support that serves as an anchor and protecting group throughout the chemical manipulations. Additionally, He, et al., *J. Org. Chem.,* 1998, 63, 5769 reports the synthesis of 5'-α-boranotriphosphates.

Preparation of other derivatized nucleosides and nucleic acids has been studied. For example, Mori. et al., *Nucleic Acids Research,* 1978, 5, 2945–2957, report phosphoroselenoate nucleic acid derivatives in which selenium replaces one of the phosphate oxygens through substitution of one of the non-bridging oxygen atoms using potassium selenocyanoate as the selenium donor. Stawinski, et al., *J. Org. Chem.,* 1994, 59, 130–136, disclose a method of synthesizing dinucleoside phosphoroselenoates through use of a selenium transferring reagent to convert nucleoside H-phosphonate and H-phosphonothioate diesters into their corresponding phosphoroselenoates and phosphorothioselenoates. Brownlee, et al., *Nucleic Acid Research,* 1995, 23, 2641–2647, report a solid phase method of synthesizing 5'-diphosphorylated oligoribonucleotides in preparing capped oligonucleotides. Nyilas, *Tetrahedron Letters,* 1997, 38, 2517–1518, disclose a one-pot synthesis of γ-amidite modified nucleoside triphosphates by opening cyclic trimetaphosphate with different amines. Krzyzanowska, et al., *Tetrahedron,* 1998, 54, 5119–5128, adapted the Ludwig, 1989, supra, method to create a one-pot procedure for synthesizing 2'-deoxyribonucleoside 5'-(α-P-borano) triphosphates.

As pharmacological agents, nucleoside triphosphates are often difficult to employ because of the hydrolytic lability of the triphosphate group. As a result, these compounds have short half lives in biological systems and often decompose too quickly to be of therapeutic value. Modified nucleoside triphosphate compounds, such as those that mimic natural analogs and have desired downstream pharmacological effects, are current pharmaceutical goals. In particular, nucleosides having modifications that increase hydrolytic stability, maintain biological activity, and exhibit low toxicity are currently desired. More efficient methods for their synthesis are also needed.

SUMMARY OF THE INVENTION

The present invention provides nucleoside triphosphate compounds of Formula I:

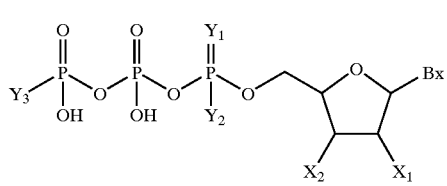

wherein:
$Y_1$ is S and $Y_2$ is $NHR_1$, $BH_3$, or SH; or
$Y_1$ is Se and $Y_2$ is SH;
$Y_3$ is $NHR_1$, OH, $C_1$–$C_{12}$ alkyl, or $C_1$–$C_{12}$ O-alkyl;
$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;

Bx is an optionally protected heterocyclic base moiety;

one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;

J is a bifunctional linking moiety; and

SM is a solid support medium.

The present invention further provides nucleoside triphosphate compounds of Formula I, wherein: $Y_1$ is O and $Y_2$ is $NHR_1$ or $Y_1$ is Se and $Y_2$ is OH, and $Y_3$, $R_1$, Bx, $X_1$, and $X_2$ are as defined above.

According to certain aspects of the present invention, nucleoside triphosphates of Formula I can be prepared according to methods comprising the step of reacting a compound of Formula III

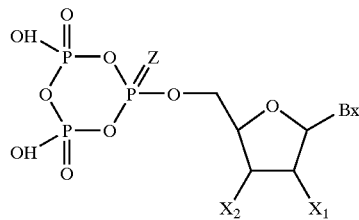

III wherein Z is $NHR_1$ or Se; with a ring-opening agent.

According to further embodiments, nucleoside triphosphates of Formula I can be prepared according to methods comprising reacting a compound of Formula III wherein Z is $NHR_1$, $BH_3$, S, or Se with a ring-opening agent comprising at least one sulfur atom.

In yet further embodiments, the present invention encompasses compounds of Formula III wherein: Z is $NHR_1$ or Se; and $R_1$, Bx, $X_1$, and $X_2$ are as defined above.

According to further embodiments, the present invention includes compounds of Formula VIII:

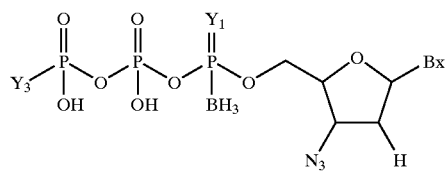

VIII wherein:

$Y_1$ is O or S;

$Y_3$ is $NHR_1$, OH, $C_1$–$C_{12}$ alkyl, or $C_1$–$C_{12}$ O-alkyl;

$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto; and Bx is adenine, thymine, cytosine, guanine, or uracil.

According to other aspects of the present invention, methods are provided for inhibiting RNA replication in a cell by contacting the cell with any of the above-recited compounds of Formula I.

In accordance with further embodiments of the present invention, methods are provided for inhibiting viral replication in a cell by contacting the cell with any of the above-recited compounds of Formula I.

According to yet further embodiments, methods are provided for treating a viral infection in a mammal by administering to the mammal an antiviral amount of any of the above-recited compound of Formula I, or a pharmaceutically acceptable salt thereof.

Other embodiments include pharmaceutical formulations comprising any of the above-recited compounds of Formula I and a pharmaceutically acceptable excipient.

DETAILED DESCRIPTION OF PREFERRED EMBODIMENTS

Figure 1:
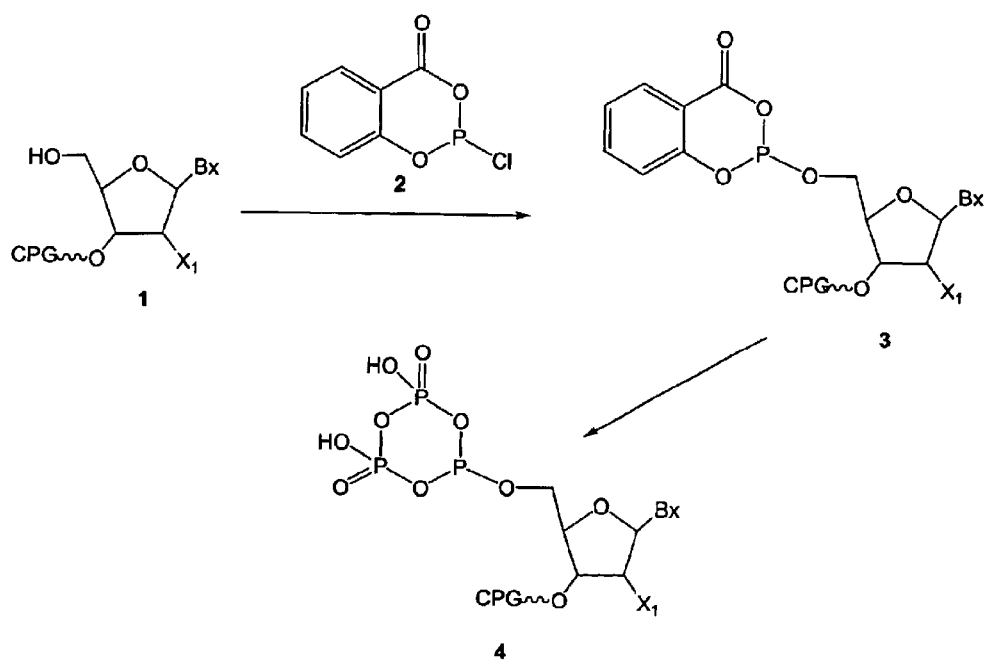
FIG. 1 is a synthesis schematic according to certain embodiments of the present invention.

The present invention includes processes for the preparation of α-modified (and/or γ-modified) nucleoside triphosphates. Synthesis of the present compounds can be carried out by oxidation of an appropriate nucleosidyl cyclotriphosphite intermediate followed by a ring-opening step. The oxidation step can be used for the introduction of substituents onto the α-P while the ring-opening step can be used for the introduction of substituents onto the γ-P.

Accordingly, the present invention provides processes for preparing nucleoside triphosphate compounds of Formula I:

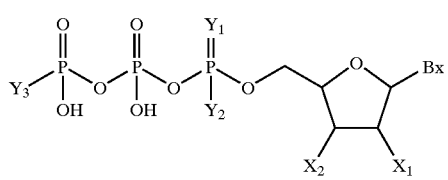

I wherein:

$Y_1$ is S and $Y_2$ is $NHR_1$, $BH_3$, or SH; or $Y_1$ is Se and $Y_2$ is SH;

$Y_3$ is $NHR_1$, OH, $C_1$–$C_{12}$ alkyl, or $C_1$–$C_{12}$ O-alkyl;

$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_2$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;

Bx is an optionally protected heterocyclic base moiety;

one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;

J is a bifunctional linking moiety; and

SM is a solid support medium:

comprising the step of reacting a compound of Formula III

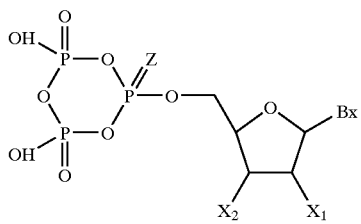

III wherein Z is $NHR_1$, $BH_3$, S, or Se;

with a ring-opening agent comprising at least one sulfur atom to give a compound of Formula I.

The present invention further provides processes for preparing nucleoside triphosphate compounds of Formula I:

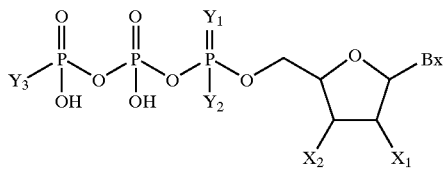

I wherein:

$Y_1$ is O and $Y_2$ is $NHR_1$; or $Y_1$ is Se and $Y_2$ is OH;

$Y_3$ is $NHR_1$, OH, $C_1$–$C_{12}$ alkyl, or $C_1$–$C_{12}$ O-alkyl;

$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;

Bx is an optionally protected heterocyclic base moiety;

one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;

J is a bifunctional linking moiety; and

SM is a solid support medium:

comprising the step of reacting a compound of Formula III

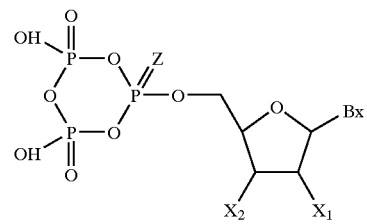

III wherein Z is $NHR_1$ or Se; with a ring-opening agent to give a compound of Formula I.

The ring-opening agent can be any reagent capable of converting the cyclotriphosphate moiety of Formula III into a linear triphosphate moiety. In some embodiments, ring-opening agents are hydrolytic reagents, effectively cleaving the ring by hydrolysis. Accordingly, some suitable ring-opening agents include water or aqueous solutions. Hydrolysis can be acid or base catalyzed. In some embodiments, ring-opening is carried out with aqueous solutions of ammonium hydroxide. Other suitable ring-opening reagents include at least one sulfur atom. According to some embodiments, at least one sulfur atom of the ring-opening agent is transferred to the α-P, resulting in, for example, nucleoside triphosphate compounds in which the α-P is substituted by a sulfur-containing group such as SH. Some suitable ring-opening agents comprising at least one sulfur atom include sulfide derivatives such as $H_2S$, $Na_2S$, $Li_2S$, $(TMS)_2S$ (trimethylsilyl sulfide), and the like. According to some embodiments, the ring-opening agent can comprise $Li_2S$. Ring-opening agents that comprise at least one sulfur atom can be combined with a suitable non-aqueous solvent system such as, for example, DMF, and/or can be combined with a solubility aid such as a crown ether, including, for example, 18-crown-6 ether.

According to the processes herein, a compound of Formula III wherein Z is $NHR_1$, $BH_3$, S, or Se can be formed by the reaction of a compound of Formula II with an oxidizing reagent.

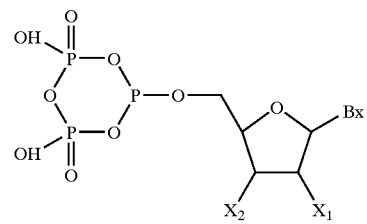

II

Suitable oxidizing reagents include those that oxidize and transfer at least one atom to the phosphite moiety of a compound of Formula II. Some suitable oxidizing reagents can include oxygen, sulfur, and selenium atom transfer agents. Sulfur atom transfer reagents can include elemental sulfur and the like. Selenium atom transfer reagents can include elemental selenium, 3H-1,2-benzothiaselenol-3-one, or the like. Other suitable oxidizing reagents can include combinations of oxidant and other compounds. For example, oxidizing reagents can comprise $I_2$ as an oxidant in combination with an amine (e.g., $NH_3$, $NH_2R_1$, etc.). Reaction of compounds of Formula II with $I_2$ and at least one amine can result in amine substitution at the α-P. Other oxidizing agents can include borane or borane-amine adducts. A suitable borane-amine adduct is, for example, borane-N,N-diisopropylethylamine complex ($BH_3$:DIPEA). Borane and borane-amine adducts can lead to borane substitution of the α-P of nucleoside triphosphates. Oxidizing agents can be dissolved or suspended in any appropriate solvent system. Non-aqueous solvent systems are suitable.

Suitable solvents useful in connection with the present processes can include 1,4-dioxane, THF (tetrahydrofuran), $(MeO)_3PO$, acetonitrile, DMF (dimethylformamide), formamide, and the like. Mixtures of carbon disulfide, pyridine, and tryiethylamine can also be used in some embodiments. Other embodiments employ solvents that comprise acetonitrile. The solvent used can also be a mixture of acetonitrile and triethylamine. Such mixture comprises from about 1% to about 30% triethylamine in acetonitrile by volume.

The oxidation step can be conducted for a time and under conditions to produce compounds of Formula III. For example, oxidation can be carried out for up to about 12 hours, 3 hours, 2 hours, or less. In other embodiments, the step can be conducted for up to about 40 minutes.

According to some embodiments of the present invention, α-modified nucleoside triphosphates are prepared using solid support (support media). Solid support typically facilitates isolation of reaction intermediates and products. Compounds of the present invention can be attached to solid support at the 2' or 3' position of the ribose moiety. Processes of the present invention can comprise the treatment of supported compounds with a cleaving reagent to cleave the compounds from solid support. Additionally, the cleaving reagent can serve to remove protecting groups from the present compounds, such as protecting groups present on the heterocyclic base moiety (Bx). An example of a suitable reagent for both deprotection and cleavage is aqueous ammonia. Optionally, processes of the present invention can include separate treatment of compounds with a deprotecting reagent to remove any protecting groups, such as might be attached to the heterocyclic base moiety.

In general, protecting groups render chemical functionality inert to specific reaction conditions, and can be appended to and removed from such functionality in a molecule. Representative protecting groups are disclosed by Beaucage, et al., *Tetrahedron*, 1992, 48, 2223. Some protecting groups can include dimethoxytrityl (DMTr), monomethoxytrityl, 9-phenylxanthen-9-yl (Pixyl) and 9-(p-methoxyphenyl)xanthen-9-yl(Mox). Numerous amine protecting groups are known in the art, and can be used, including the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschrnann, et al., *J. Org. Chem.* 1977, 42, 3286 and Atherton, et al., *The Peptides*, Gross and Meienhofer, Eds, Academic Press; New York, 1983; Vol. 9 pp. 1–38). For example, it is known that the Boc group can protect an amine group from base and from reducing conditions but that it can be removed with acid. Methods for protection and deprotection are well known in the art.

In further embodiments of the present invention, α-modified triphosphate nucleosides are provided. α-Modified nucleoside triphosphates can also comprise substitution at the γ-position of the triphosphate moiety. Accordingly, the present invention includes compounds of Formula I, wherein:

$Y_1$ is S and $Y_2$ is $NHR_1$, $BH_3$, or SH; or
$Y_1$ is Se and $Y_2$ is SH;
$Y_3$ is $NHR_1$, OH, $C_1$–$C_{12}$ alkyl, or $C_1$–$C_{12}$ O-alkyl;
$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;
Bx is an optionally protected heterocyclic base moiety;
one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;
J is a bifunctional linking moiety; and
SM is a solid support medium.

Other embodiments of the present invention include compounds of Formula I, wherein:
$Y_1$ is O and $Y_2$ is $BH_3$; or
$Y_1$ is Se and $Y_2$ is OH;
$Y_3$ is $NHR_1$, OH, $C_1$–$C_{12}$ alkyl, or $C_1$–$C_{12}$ O-alkyl;
$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylamninoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;
Bx is an optionally protected heterocyclic base moiety;
one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;
J is a bifunctional linking moiety; and
SM is a solid support medium.

As used herein, the term "alkyl" includes but is not limited to straight chain, branch chain, and alicyclic hydrocarbon groups. Alkyl groups of the present invention can be substituted. Representative alkyl substituents are disclosed in U.S. Pat. No. 5,212,295, which is hereby incorporated by reference in its entirety. The term "alkenyl" refers to alkyl groups having one or more double carbon-carbon bonds. The term "alkynyl" refers to alkyl groups having one or more triple carbon-carbon bonds. As used herein, the term "aralkyl" denotes alkyl groups which bear aryl groups. An example of an aralkyl group is benzyl. The term "alkylaryl" denotes aryl groups which bear alkyl groups. An example of an alkylaryl group is methylphenyl. As used herein the term "aryl" denotes aromatic cyclic groups including but not limited to phenyl, naphthyl, anthracyl, phenanthryl, and pyrenyl. In general, the term "hetero" denotes an atom other than carbon, preferably, but not exclusively, N, O, or S. Accordingly, the term "heterocycloalkyl" denotes an alkyl ring system having one or more heteroatoms. Some heterocycloalkyl groups include, for example, morpholino groups. As used herein, the term "heteroaryl" denotes an aryl group comprising one or more heteroatoms. An example of a heteroaryl group includes pyridyl.

In some embodiments of the present invention, amino functional groups are covalently attached to the α-phosphorous of nucleoside triphosphates. In other embodiments, an amino functional group is covalently attached to the γ-posphorous of the α-modified triphosphate nucleoside. An amino functional group according to the present invention includes moieties having the formula —$NHR_1$, where $R_1$ includes, for example, hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl. Substituted moieties can comprise one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto.

A heterocyclic base moiety (often referred to in the art simply as a "base" or a "nucleobase") amenable to the present invention includes both naturally and non-naturally occurring nucleobases. The heterocyclic base moiety further can be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-Me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-aza uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993, each of which is incorporated herein by reference in its entirety.

Certain heterocyclic base moieties are particularly useful for increasing the binding affinity of the oligomeric compounds that incorporate them to complementary targets. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6–1.2° C. Duplex stability can also be enhanced with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,808,027, certain of which are commonly owned, and each of which is herein incorporated by reference.

Some sugar substituent groups amenable to the present invention include $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkyny O-alkylamino, O-alkylalkoxy, O-alkylaminoalkyl, O-alkyl imidazole, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen (e.g., fluoro, bromo, chloro, iodo), keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, heterocycle, carbocycle, polyamine, polyamide, polyalkylene glycol, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. Pat. No. 6,166,197, which is incorporated herein by reference in its entirety.

Additional sugar substituent groups amenable to the present invention include —SR and —$NR_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, which is incorporated herein by reference in its entirety. The incorporation of 2'-SR monomer synthons are disclosed by Hamm, et al., *J. Org. Chem.*, 1997, 62, 3415–3420, and 2'-$NR_2$ nucleosides are disclosed by Goettingen, M., *J. Org. Chem.*, 1996, 61, 73–6281 and Polushin et al., *Tetrahedron Lett.*, 1996, 37, 3227–3230, each of which are incorporated herein by reference in their entireties.

Further sugar substituent groups can have one of formula IV or V:

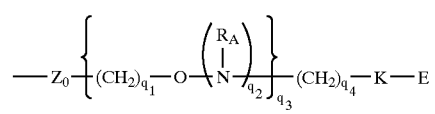

IV

-continued

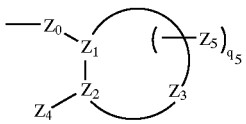

wherein:
Z₀ is O, S or NH;
K is a single bond, O or C(=O);
E is $C_1$–$C_{10}$ alkyl, $N(R_A)(R_2)$, $N(R_A)(R_5)$, $N=C(R_A)(R_2)$, $N=C(R_A)(R_5)$ or has one of formula VI or VII;

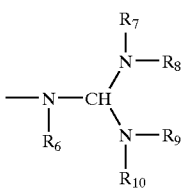

VI

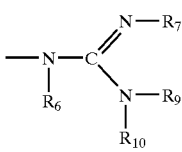

VII wherein:
each $R_6$, $R_7$, $R_8$, $R_9$ and $R_{10}$ is, independently, hydrogen, $C(O)R_{11}$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the sugar substituent groups are selected from hydroxyl, amino, alkoxy, carboxy, benzyl, phenyl, nitro, thiol, thioalkoxy, halogen, alkyl, aryl, alkenyl and alkynyl;
or optionally, $R_7$ and $R_8$, together form a phthalimido moiety with the nitrogen atom to which they are attached;
or optionally, $R_9$ and $R_{10}$, together form a phthalimido moiety with the nitrogen atom to which they are attached;
each $R_{11}$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
$R_5$ is T-L,
T is a bond or a linking moiety;
L is a chemical functional group, a conjugate group or a solid support material;
each $R_A$ and $R_2$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)$ $(R_4)$, guanidino or acyl where said acyl is an acid amide or an ester;
or $R_A$ and $R_2$, together, are a nitrogen protecting group or are joined in a ring structure that optionally includes an additional heteroatom selected from N and O;
or $R_A$, T and L, together, are a chemical functional group;
each $R_3$ and $R_4$ is, independently, H, $C_1$–$C_{10}$ alkyl, a nitrogen protecting group, or $R_3$ and $R_4$, together, are a nitrogen protecting group;
or $R_3$ and $R_4$ are joined in a ring structure that optionally includes an additional heteroatom selected from N and O;

$Z_4$ is OX, SX, or $N(X)_2$;
each X is, independently, H, $C_1$–$C_8$ alkyl, $C_1$–$C_8$ haloalkyl, $C(=NH)N(H)R_5$, $C(=O)N(H)R_5$ or $OC(=O)N(H)R_5$;
$R_5$ is H or $C_1$–$C_8$ alkyl;
$Z_1$, $Z_2$ and $Z_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;
$Z_5$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_A)(R_2)OR_1$, halo, $SR_A$ or CN;
each $q_1$ is, independently, an integer from 1 to 10;
each $q_2$ is, independently, 0 or 1;
$q_3$ is 0 or an integer from 1 to 10;
$q_4$ is an integer from 1 to 10;
$q_5$ is from 0, 1 or 2; and
provided that when $q_3$ is 0, $q_4$ is greater than 1.

Representative sugar substituent groups of Formula IV are disclosed in U.S. Pat. No. 6,172,209, which is incorporated herein by reference in its entirety.

Representative cyclic sugar substituent groups of Formula V are disclosed in U.S. Pat. No. 6,271,358, which is hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, $O(CH_2)_nON[(CH_2)_nCH_3)]_2$ (where n and m are from 1 to about 10), $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino and substituted silyl. Another particularly preferred modification includes 2'-methoxyethoxy (2'-O—$CH_2CH_2OCH_3$ or 2'-MOE, as described in, e.g., Martin et al., *Helv. Chim. Acta*, 1995, 78, 486, which is incorporated herein by reference in its entirety). A further preferred sugar substituent group is 2'-dimethylaminooxyethoxy ($O(CH_2)_2ON(CH_3)_2$), also known as 2'-DMAOE. Representative aminooxy sugar substituent groups are described in co-owned U.S. Pat. No. 6,576,752 entitled "Aminooxy-Functionalized Oligomers;" and U.S. Pat. No. 6,639,062 entitled "Aminooxy-Functionalized Oligomers and Methods for Making Same," each of which is herein incorporated by reference in its entirety.

Other preferred modifications include 2'-methoxy (2'-O—$CH_3$), 2'-aminopropoxy (2'-$OCH_2CH_2CH_2NH_2$), and 2'-fluoro (2'-F). The configuration of the sugar substituent group is also variable such as at the 2'-position. In addition to the ribose configuration, the arabinose configuration is also amenable to the present invention. Arabinose modifications are known to those skilled in the art and include procedures described in for example, Damha et al., *J.A.C.S.*, 1998, 120, 12976–12977; Wilds, et al., *Bioconjugate Chem.*, 1999, 10, 299–305; and Wilds, et al., *Nucleic Acids Res.*, 2000, 28(18), 3625–363.

Similar modifications can also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5'-position at a 5'-terminus. Oligomers can also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, certain of which are commonly owned, and each of which is herein incorporated by reference in its entirety.

Representative guanidino sugar substituent groups that are shown in formula VI and VII are disclosed in co-owned U.S. Pat. No. 6,593,466 entitled "Functionalized Oligomers," filed Jul. 7, 1999, hereby incorporated by reference in its entirety.

Representative acetamido sugar substituent groups are disclosed in U.S. Pat. No. 6,147,200, entitled "2'-O-Acetamido Modified Monomers and Oligomers", filed Aug. 19, 1999, also identified by attorney docket number ISIS-4071, which is incorporated herein by reference in its entirety.

Representative dimethylaminoethyloxyethyl sugar substituent groups are disclosed in WO 00/08044, which is incorporated herein by reference in its entirety.

As used herein, a "bifunctional linking moiety" refers to a hydrocarbyl chain which connects the monomers and oligomers of the invention to a support medium. A preferred linking moiety is a succinyl group. Other linking moieties include, but are not limited to, substituted or unsubstituted $C_1$–$C_{10}$ alkyl, substituted or unsubstituted $C_2$–$C_{10}$ alkenyl or substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl. Other linking moieties are known in the art and are equally amenable to the present invention.

In one embodiment of the present invention modified triphosphate nucleotides are prepared with the nucleoside portion linked to a support media. Preferred attachments are via the 2' or 3'-position of the sugar portion of the nucleoside but other points of attachment such as via the heterocyclic base moiety are known in the art and amenable to the present invention.

Preferred support media is insoluble and allows all of the reactants to be easily removed by washing with an appropriate solvent. However, soluble or variable soluble support media can also be used. Such support permits variable solubility of the nucleoside-bound synthon in different solvents thereby allowing variable solubility. Traditional solid supports are insoluble and are routinely placed in a reaction vessel while reagents and solvents react and or wash the growing chain until cleavage frees the final oligomer. More recent approaches have introduced soluble supports including soluble polymer supports to allow precipitating and dissolving of the synthon at desired points in the synthesis (see, e.g., Gravert et al., *Chem. Rev.,* 1997, 97, 489–510).

Representative support media that are amenable to the methods of the present invention include without limitation: controlled pore glass (CPG); oxalyl-controlled pore glass (see, e.g., Alul, et al., *Nucleic Acids Research* 1991, 19, 1527); TENTAGEL Support, (see, e.g., Wright, et al., *Tetrahedron Letters* 1993, 34, 3373); or POROS, a copolymer of polystyrene/divinylbenzene available from Perceptive Biosystems. The use of a soluble support media, poly (ethylene glycol), with molecular weights between 5 and 20 kDa, for large-scale synthesis of oligonucleotides is described in, Bonora et al., *Organic Process Research & Development,* 2000, 4, 225–231.

Many hydroxyl protecting groups known in the art are amenable to use in the present invention. Examples of certain preferred hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Further hydroxyl protecting groups can include groups having the formula: —C(R')(R")(R'"), wherein each of R', R" and R'" is an unsubstituted or mono-substituted aryl or heteroaryl group selected from phenyl, naphthyl, anthracyl, and five or six membered heterocylic rings with a single heteroatom selected from N, O and S, or two N heteroatoms, including quinolyl, furyl, and thienyl; where the substituent is selected from halo (i.e., F, Cl, Br, and I), nitro, $C_1$–$C_4$-alkyl or alkoxy, and aryl, aralkyl and cycloalkyl containing up to 10 carbon atoms; and wherein R" and R'" can each also be $C_1$–$C_4$-alkyl or aralkyl or cycloalkyl containing up to 10 carbon atoms.

Further embodiments of the present invention encompass compounds of Formula III

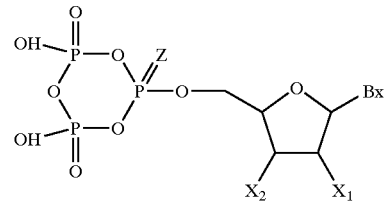

III wherein:

Z is $NHR_1$ or Se:

$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;

Bx is an optionally protected heterocyclic base moiety;

one of $X_1$ and $X_2$ is H, hydroxyl, a protected hydroxyl, or a sugar substituent group and the other of $X_1$ and $X_2$ is hydroxyl, a protected hydroxyl, or azido, -O-J-SM;

J is a bifunctional linking moiety; and

SM is a solid support medium.

Other embodiments include compounds of Formula VIII:

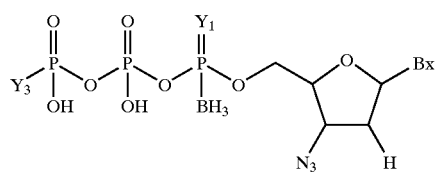

VIII wherein:
$Y_1$ is O or S;
$Y_3$ is $NHR_1$, OH, $C_1$–$C_{12}$ alkyl, or $C_1$–$C_{12}$ O-alkyl;
$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto; and
Bx is adenine, thymine, cytosine, guanine, or uracil.

Some examples of compounds of Formula VIII include those where Bx is thymine, $Y_1$ is O, and/or $Y_3$ is OH.

The compounds described herein, and derivatives thereof, have well known utility to those skilled in the art. For example, α-phosphate modified nucleoside triphosphates can be used as a new class of model compounds for studies related to enzyme functions and mechanisms of action. Such studies can include, for instance, the stereochemical courses of a wide variety of NTP-based enyzmatic reactions and metal ion dependence for diastereomeric forms of α-P substituted analogues of nucleoside 5'-triphosphates. These compounds can also be used in construction of potential therapeutic agents and pro-drugs, working as reversible and irreversible inhibitors, transition state analogues, suicide substrates, and spectroscopic probes. α-Modified nucleoside triphosphates can also be used for enzymatic site-specific synthesis of oligonucleotides (both DNA and RNA) carrying modified internucleotidic linkages. The compounds described herein can be further used in direct nucleic acid sequencing by their incorporation into PCR products followed by chemical degradation to reveal their sequence positions.

According to further aspects of the present invention, the above compounds can be used for the inhibition of the enzymatic activity of enzymes having nucleoside triphosphates as substrates. For example, nucleoside triphosphates are substrates of many enzymes such as polymerases and reverse transcriptases. Polymerases can include both DNA and RNA polymerases, including, for example, RNA-dependent RNA polymerases. Accordingly, the methods of the present invention encompass methods for inhibiting enzyme activity comprising the step of contacting the enzyme with at least one compound of the present invention for a time and under conditions effective to inhibit activity of the enzyme. Contacting of enzyme can be carried out in vivo or in vitro.

The present invention further includes methods for inhibiting RNA replication in a cell. The methods comprise the step of contacting at least one compound of the present invention with a cell. The cell can be infected with a virus and/or possess viral RNA. Contacting can be carried out in vivo or in vitro.

Methods for inhibiting viral replication in a cell are also encompassed by the present invention. The methods comprise the step of contacting at least one compound of the present invention with a cell containing a virus. Inhibition of viral replication can be determined by comparison of viral counts for untreated and treated infected cells.

The present invention also includes methods of treating a viral infection in a mammal. The methods include administering to a mammal, such as a human, an antiviral amount of at least one compound of the present invention. Some viral infections can include, for example, infection by any one of HCV, HIV, herpes, influenza, or other viruses. An antiviral amount can be defined as the amount of active compound required to slow the progression of viral replication or reduce viral load from that which would otherwise occur without administration of the compound. Or, it is an amount of active compound required to slow the progression or reduce the intensity of symptoms resulting from viral infection or elimination thereof.

Administration of compounds to a mammal can be carried out by any method known in the art. For example, the present compounds can be injected parenterally, i.e., intramuscularly, intravenously, or subcutaneously. For parenteral administration, the compound can be used in the form of sterile solutions containing other solutes, for example, sufficient saline or glucose to make the solution isotonic.

The compounds can be administered orally in the form of tablets, capsules, or granules containing suitable conventional carriers or excipients such as starch, lactose, white sugar etc. The compounds can be administered orally in the form of solutions that can contain coloring and/or flavoring agents. The compounds can also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound.

The solid oral compositions can be prepared by conventional methods of blending, filling, tableting, etc. Repeated blending operations can be used to distribute the active agent throughout those compositions employing large quantities of fillers. Such operations are conventional in the art. The tablets can be coated according to methods well known in normal pharmaceutical practice, in particular with an enteric coating.

Oral liquid preparations can be in the form of emulsions, syrups, or elixirs, or can be presented as a dry product for reconstitution with water or other suitable vehicle before use. Such liquid preparations can contain conventional additives. For example, suspending agents can be used, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acacia; non-aqueous vehicles (which can include edible oils), such as almond oil, fractionated coconut oil, oily esters selected from the group consisting of glycerin, propylene glycol, ethylene glycol, and ethyl alcohol; preservatives, for instance methyl para-hydroxybenzoate, ethyl para-hydroxybenzoate, n-propyl para-hydroxybenzoate, or n-butyl para-hydroxybenzoate of sorbic acid; and, if desired, conventional flavoring or coloring agents.

For parenteral administration, fluid unit dosage forms can be prepared by utilizing the compound and a sterile vehicle, and, depending on the concentration employed, can be either suspended or dissolved in the vehicle. Once in solution, the compound can be injected and filter sterilized before filling a suitable vial or ampoule and subsequently sealing the carrier or storage package. Adjuvants, such as a local anesthetic, a preservative or a buffering agent, can be dissolved in the vehicle prior to use. Stability of the pharmaceutical composition can be enhanced by freezing the composition after filling the vial and removing the water under vacuum, (e.g., freeze-drying the composition). Parenteral suspensions can be prepared in substantially the same manner, except that the peptide should be suspended in the vehicle rather than being dissolved, and, further, sterilization is not achievable by filtration. The compound can be sterilized, however, by exposing it to ethylene oxide before suspending it in the sterile vehicle. A surfactant or wetting solution can be advantageously included in the composition to facilitate uniform distribution of the compound.

Some compounds of the present invention can form pharmaceutically acceptable salts. For example, compounds with basic substituents such as an amino group form salts with weaker acids. Examples of suitable acids for salt formation include hydrochloric, sulfuric, phosphoric, acetic, citric, oxalic, malonic, salicylic, malic, fumaric, succinic, ascorbic, maleic, methanesulfonic, trifluoroacetic and other mineral and carboxylic acids well known to those skilled in the art. The salts are prepared by contacting the free base form with a sufficient amount of the desired acid to produce a salt in a conventional manner. The free base forms can be regenerated by treating the salt with a suitable diluted aqueous base solution such as dilute aqueous sodium hydroxide, potassium carbonate, ammonia and sodium bicarbonate. The free base forms can differ from their respective salt forms somewhat in certain physical properties, such as solubility in polar solvents, but the acid and base salts are otherwise equivalent to their respective free base forms for purposes of the present invention.

The methods of the present invention can also comprise the step of administering to a mammal an agent selected from an immunomodulatory agent, an antiviral agent, a protease inhibitor, a helicase inhibitor, a polymerase inhibitor, or a metalloprotease inhibitor. Such additional agents can be administered to the mammal prior to, concurrently with, or following the administration of a compound of the present invention.

EXAMPLES

In connection with the procedures described below, the following experimental parameters were employed. The phosphitylating reagent 2-chloro-4H-1,3,2-benzodioxaphosphorin-4-one was purchased from Aldrich and used as 1M solution in dioxane (always prepared fresh prior to use). The solvents dioxane, pyridine, acetonitirile, N,N-dimethyl-formamide (DMF) and tetrahydrofuran (THF) were purchased from Aldrich as anhydrous and used without further purification unless otherwise stated. Solvents were stored over molecular sieves 4 Å. Tri-n-butylamine, n-butylamine, n-propylamine and methylamine (2 M solutions in THF) were dried and stored over 4 Å molecular sieves. The bis(tri-n-butylammonium) pyrophosphate was obtained from Fluka and stored as a 0.5M solution in DMF over 4 Å molecular sieves. TLC was performed on HPTLC Fertigplatten Si 5000F (Merck Darmstad) and detected by visualization under short wave UV light or by heating the plate at 110° C. after spraying with 5% solution of sulfuric acid in ethanol.

$^{31}$P NMR spectra were recorded on a Varian spectrometer operating at 400 MHz with broad band decoupling. Spectra of intermediates synthesized in solution were recorded after addition of anhydrous deuterated chloroform ($CDCl_3$). Reversed phase HPLC was achieved with a Gilson (Middleton, Wis.) quaternary pump system, consisting of 4 pumps, with dual wavelength detector. Components of the HPLC system were controlled by a Gilson's Uniport software package. A Phenomenex (Torrance, Calif.) Luna (C-18 (2)), 250×21.2 mm, 5-um particle size, column and a linear gradient from 1% to 25% of methanol in 60 minutes at constant pH 7, concentration TEAA (50 mM) was used to purify the synthesized nucleoside triphosphates. The flow rate was 10 mL/min.

The mass spectra of the purified triphosphates was determined using on-line HPLC mass spectrometry on a Hewlett-Packard (Palo Alto, Calif.) MSD 1100.

RP HPLC was performed on a Phenomenex Luna (C-18 (2)), 150×2 mm, plus 30×2 mm guard column, 3-$\mu$m particle size. A 0 to 50% linear gradient of acetonitrile in 20 mM TEAA (pH 7) was performed in series with mass spectra detection in the negative ionization mode. Nitrogen gas and a pneumatic nebulizer were used to generate the electrospray. The mass range of 150–900 was sampled. Molecular masses were determined using the HP Chemstation analysis package.

Example 1

Attachment of Nucleosides to Solid Support

Nucleosides were protected if necessary and attached to support media using standard procedures. A fully protected nucleoside is selected having a free hydroxyl group at the 2' or 3'-position. A typical selection is a 5'-DMT-nucleoside having any exocyclic amino groups protected as the N-acyl group. The free hydroxyl group is attached to an amino functionalized solid support (e.g., controlled pore glass (CPG) or polystyrene using a succinate linking group). A general procedure is illustrated in by Sproat et al., *Oligonucleotides and Analogues*, Eckstein, F., Ed., IRL Press, Oxford. 1991; pp.49–86.

Example 2

Procedure for the Synthesis of Solid Support Bound Cyclic Triphosphite(4)

An example of this procedure is shown in FIG. 1. Solid support derivatized with a selected nucleoside (as per Example 1, 100 $\mu$moles) was placed in a small glass column fitted with a septum and equipped with a glass sinter and tap at the bottom (volume about 16 mL). The support was treated with a 3% solution of trichloroacetic acid in dichloromethane (2×10 mL) for 2 minutes to remove the 5'-protecting group. The solid support was washed with dichloromethane (10 mL), dry acetonitrile (10 mL), a dry mixture of pyridine and dioxane (10 mL, 1:3, v/v). A fresh 1M solution of 2-chloro-4H-1.3.2-benzodioxaphosphorin-4-one in dry dioxane (4 mL) was then added to the support suspended in dry pyridine/dioxane (8 mL, 1:3, v/v). The reactor was gently agitated for 20 minutes, the phosphitylating solution removed under an atmosphere of argon and the support washed with a dry mixture of pyridine and dioxane (10 mL, 1:3, v/v) followed by acetonitrile (10 mL) and N,N-dimethylformamide (10 mL). A mixture of 0.4M bis(tributylammonium) pyrophosphate in dry DMF (6 mL) and tri-n-butylamine (2 mL) was added to the reactor with agitation for 40 minutes. The support was washed with dry N,N-dimethylformamide (10 mL), dry acetonitrile (10 mL) and dry tetrahydrofuran (10 mL) to give the support bound cyclic triphosphate nucleoside (4, FIG. 1).

Example 3

Procedure for the Synthesis or α-amino Triphosphate Nucleosides

Figure 2:
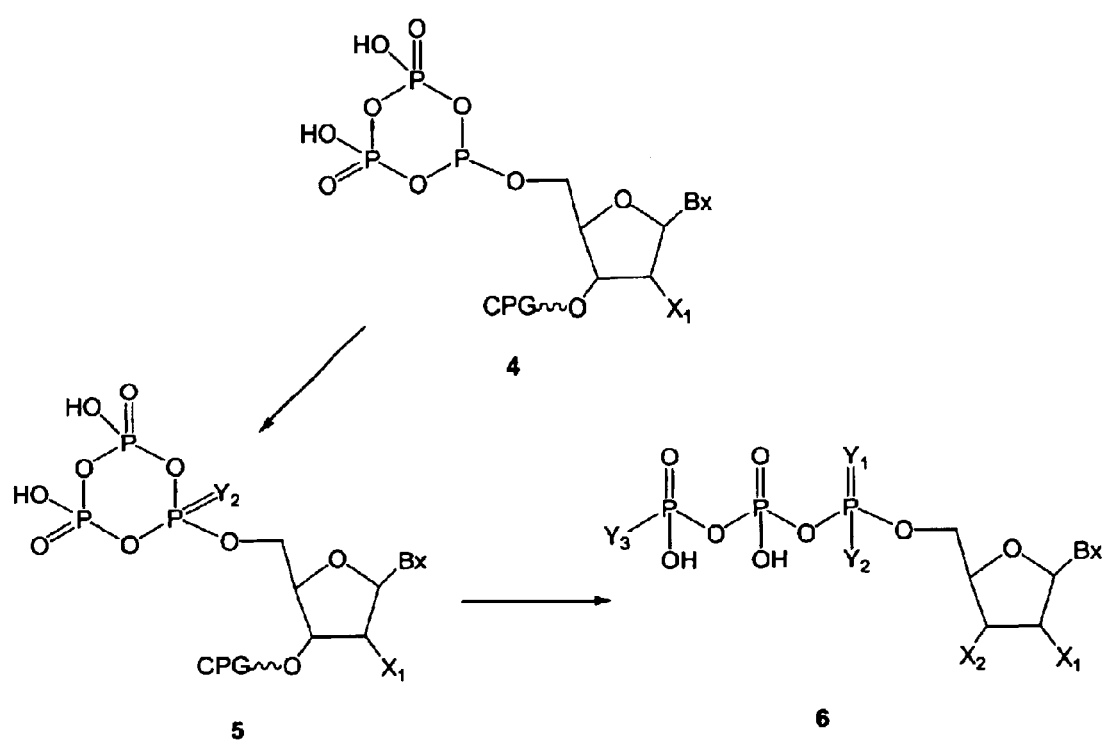
FIG. 2 is a synthesis schematic according to certain embodiments of the present invention.
Figure 3:
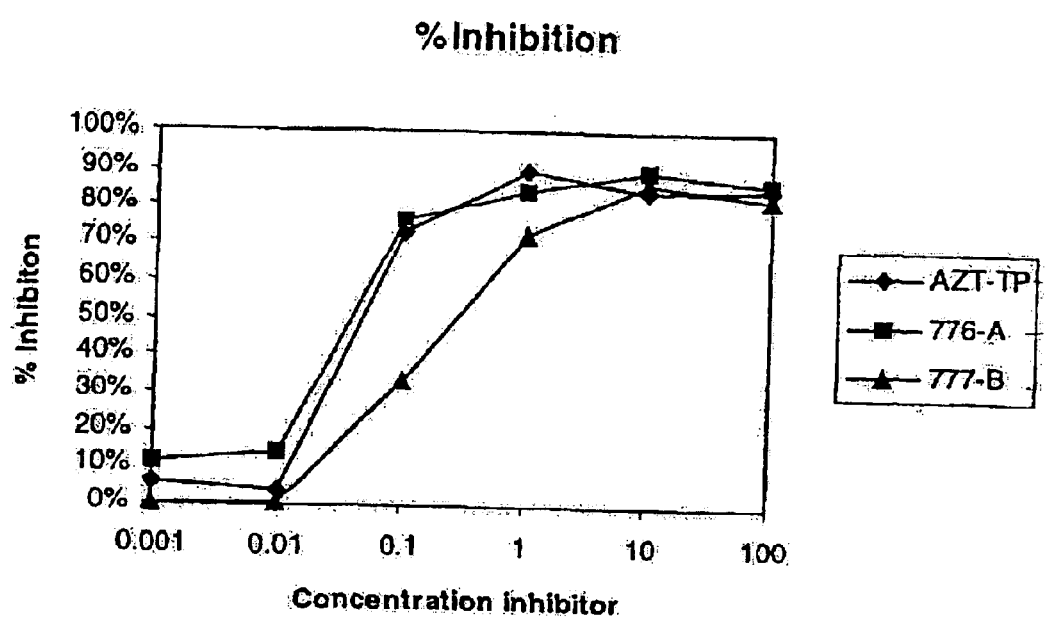
FIG. 3 shows a plot of percent inhibition of HIV-RT v. concentration of inhibitor (mM) for various compounds of the present invention (♦denotes compound 1 of Table 5, ■ denotes compound 2 of Table 5, and ▲denotes compound 3 of Table 5).

An example of this procedure is shown in FIG. 2. The cyclic triphosphite (4, Example 2) was oxidized using iodine and a primary amine, such as an alkylamine. The selected primary amine (4 mL) was suspended in a solution of iodine in tetrahydrofuran (224 mg in 5 mL). The solid support was treated with the oxidation mixture containing the primary amine and agitated for 40 minutes at 25° C. Excess oxidation mixture was removed by extensive washing with dry tetrahydrofuran (10 mL) and dry acetonitrile (10 mL). Oxidized intermediate (5) was hydrolized with water (5 mL at 25° C. for 90 minutes). The α-amino modified nucleoside triphosphate was cleaved and deprotected by treating the solid support with 25% aqueous ammonia in a sealed glass vial (15 hours at 25° C. and 2 hours at 55° C.).

The cooled ammoniacal solution of crude α-amino modified nucleoside triphosphate was evaporated to dryness. The residue was dissolved in a 0.2 M solution of triethylammonium bicarbonate buffer (pH=7) and purified by reverse phase and ion exchange HPLC to give the α-amino triphosphate nucleoside (6).

Example 4

Analytical Data for Selected α-amino Modified Nucleoside Triphosphates

The following compounds were prepared generally according to the procedures of Example 3.

2'-O-Methyl guanosine-5'-(α-P-(N-methyl) triphosphate)

$^{13}$C NMR (D$_2$O): (isomer I Sp) δ=159.13 (C-6); 154.21 (C-2); 151.92 (C-4); 138.25 (C-8); 116.26 (C-5); 85.4 (C-1'); 84.46 (C-4'); 82.54 (C-2'); 69.2 (C-3'); 65.51 (C-5'); and 58.3 (OCH$_3$).

$^{13}$C NMR (D$_2$O): (isomer II Rp) δ=159.09 (C-6); 154.23 (C-2); 151.91 (C-4); 138.05 (C-8); 116.21 (C-5); 85.5 (C-1'); 84.46 (C-4'); 82.6 (C-2'); 69.18 (C-3'); 65.82 (C-5'); and 58.3 (OCH$_3$).

$^{31}$P NMR (D$_2$O): δ=+33.71 (d, 1P, α-P, isomer I (Sp)), +33.58 (d, 1P, α-P, isomer II (Rp)), -10.94 (d, 1P, γ, P), -24.69 (dd, 1P, β-P)

Molecular weights for Rp and Sp stereoisomers were determined by LC-HPLC mass spectrometry (Hewlett-Packard MSD 1100) using a Luna (C-18(2)) column, 150×2 mm, 3-μm particle size and 0–50% gradient of MeCN in 20 mM TEAA (pH 7). The mass spectra detection was performed in the negative ionization mode. Molecular masses were determined using the HP Chemstation analysis package and were equal: 599.9 (isomer I) and 599.9 (isomer II). Calculated MW=600.17.

2'-O-Methyl guanosine-5'-(α-P-(N-butyl)triphosphate)

$^{13}$C NMR (D$_2$O): δ=166.74 (C-6); 151.9 (C-2); 137.62 (C-5); 111.94 (C-4); 85.63 (C-1')+85.05 (C-2'); 70.94 (C-3'); 65.49(C-5'); 59.15(OMe); 38.85 (C-2'); 41.66 (C$_1$—NH); 33.26 (C$_2$—NH); 19.67 (C$_3$—NH); 13.37 (C$_4$—NH); and 12.5 (C$_5$—CH$_3$).

$^{31}$P NMR (D$_2$O): δ=-0.39 (d, 1P, α-P), -11.41 (d, 1P, γ, P), and -22.64 (dd, 1P, β-P).

2'-Deoxythymidine-5'-(α-P-(amino triphosphate)

$^{13}$C NMR (D$_2$O): δ=166.9 (C-6); 152.1 (C-2); 137.74 (C-5); 112.12 (C-4); 85.82+85.73 (C-1'+C-2'); 71.3 (C-3'); 65.7(C-5'); 59.15 (OMe); 38.85 (C-2'); and 12.5 (C$_5$—CH$_3$).

$^{31}$P NMR (D$_2$O): δ=0.11 (d, 1P, α-P), -10.84 (d, 1P, γ, P), and -22.6 (dd, 1P, β-P).

Listed in Table 1 are α-amino triphosphate nucleosides of Formula I (Y$_1$=NHR$_1$) prepared by the procedures described above.

TABLE 1

α-Amino Triphosphate Nucleosides of Formula I (Y$_1$ = NHR$_1$)[a]

| R$_1$ | Bx | X$_1$ |
|---|---|---|
| —CH$_3$ | G$^{1Bu}$, C$^{Bz}$ or T | H or —OMe |
| —CH$_2$CH$_2$CH$_3$ | G$^{1Bu}$, C$^{Bz}$ or T | H or —OMe |
| —CH$_2$CH$_2$CH$_2$CH$_3$ | G$^{1Bu}$, C$^{Bz}$ or T | H or —OMe |
| —H | G$^{1Bu}$, C$^{Bz}$ or T | H or —OMe |

[a]Y$_2$ = OH, Y$_3$ = OH, and X$_2$ = OH

Example 5

Procedure for the Synthesis of α-Selenotriphosphate Nucleosides

Solid support bound cyclic triphosphite nucleoside (4, FIG. 1) was prepared generally as illustrated in Example 2 above. The oxidation of the cyclic triphosphite nucleoside was carried out using a 0.2 M solution of 3H,-1,2-benzothiaselenol-3-one in acetonitrile (8 mL) for 3 hours, followed by washing with acetonitrile (3×15 mL). The oxidized material was hydrolyzed with a mixture of water and acetonitrile (9/1, v/v, 8 mL) for 90 minutes, followed by washing with acetonitrile, methanol and dichloromethane (15 mL of each). The longer hydrolysis time proved to be necessary as the α-seleno compound was less reactive compared with the α-sulfur analogue (α-S-analogue was hydrolyzed completely in 30 minutes). The solid support was dried using a stream of dry nitrogen and removed from the reactor. The product was cleaved from the solid support using concentrated ammonia in a closed glass vial (for 12 hours at 25° C. and 3 hours at 55° C.). The α-Se-nucleoside triphosphate was obtained as essentially equal amounts of Rp and Sp stereoisomers. These stereoisomers were separated using ion-exchange and reverse-phase HPLC. The ion-exchange HPLC purification was preformed using MonoQ column (Pharmacia), 100×30 mm, and the following gradient: 0–0.72M NaCl at constant Tris (20 mM, pH 7), flow rate 6.5 mL/min. R$_t$ for the stereoisomers was 17.7 minutes. The RP-HPLC separations were performed using a Luna (C-18(2)) column, 250×21.2 mm (Phenomenex, Calif.), 5-μm particle size column using linear gradient of MeOH (1%–25%) in 60 minutes, at constant TEAA (pH 7, 50 mM), flow rate 10 mL/minutes. The retention times were 45.6 and 50 minutes for the Sp and Rp isomers respectively.

$^{13}$C NMR (D$_2$O): (isomer I Sp) δ=159.13 (C-6); 154.21 (C-2); 151.92 (C-4); 138.25 (C-8); 116.26 (C-5); 85.4 (C-1'); 84.46 (C-4'); 82.54 (C-2'); 69.2 (C-3'); 65.51 (C-5'); 58.3 (OCH$_3$); (isomer II) δ=159.09 (C-6); 154.23 (C-2); 151.91 (C-4); 138.05 (C-8); 116.21 (C-5); 85.5 (C-1'); 84.46 (C-4'); 82.6 (C-2'); 69.18 (C-3'); 65.82 (C-5'); and 58.3 (OCH$_3$).

$^{31}$P NMR (D$_2$O): δ=+33.71 (d, 1P, α-P, isomer I (Sp)), +33.58 (d, 1P, α-P, isomer II (Rp)), -10.94 (d, 1P, γ, P), and -24.69 (dd, 1P, β-P).

Molecular weight (MW) for Rp and Sp stereoisomers were determined using LC-HPLC mass spectrometry (Hewlett-Packard MSD 1100) using Luna (C-18(2)) column, 150×2 mm, 3-μm particle size and 0–50% gradient of MeCN in 20 mM TEAA (pH 7). The mass spectra detection was performed in the negative ionization mode. Molecular masses were determined using the HP Chemstation analysis package and were equal: 599.9 (isomer I) and 599.9 (isomer II). Calculated MW=600.17.

Example 6

Procedure for the Synthesis of α-Boranotriphosphate Nucleosides

Solid support bound cyclic triphosphite nucleoside (4, FIG. 1) was prepared generally as illustrated in Example 2 above. The oxidation of the cyclic triphosphite nucleoside was carried out using borane-N,N-diisopropylethylamine complex. The reaction mixture was agitated for 180 minutes at 25° C. and the oxidation reagent was removed by repeated washing with dry acetonitrile (20 mL) and DMF (10 mL). The oxidized intermediate was hydrolized with water (5 mL at 25° C. for 90 minutes). The α-borano modified nucleoside triphosphate was cleaved and deprotected by treating the solid support with 25% aqueous ammonia in a sealed glass vial (15 hours at 25° C. and 2 hours at 55° C.). The cooled ammonia solution of crude α-amino modified nucleoside triphosphate was evaporated to dryness. The residue was dissolved in a 0.2M solution of triethylammonium bicarbonate buffer (pH=7) and purified by reverse phase and ion exchange HPLC to give the α-amino triphosphate nucleoside (see Structure 6 of FIG. 2).

Example 7

Synthesis of 2'-deoxythymidine-3'-azido-5'-(α-P-(borano)triphosphate)

3'-Azido-3'-deoxythymidine (azidothymidine) (0.5 mmol, Sigma) in 50 mL reaction flask was dried by co-evaporation with anhydrous pyridine (2×15 mL). The nucleoside was dissolved in anhydrous pyridine (0.25 mL) and anhydrous dimethylformamide (DMF) (1.9 mL) in a reaction flask under an atmosphere of argon. A fresh 1 M solution of 2-chloro-4H-1.3.2-benzodioxaphosphorin-4-one in dry dioxane (0.5 mL) was added through the rubber septum into the flask with stirring. After 15 minutes an aliquot from the reaction mixture was analyzed using $^{31}$P NMR. Formation of the cyclic intermediate was confirmed by appearance of two peaks at around 125 ppm. A mixture of 0.5 M bis(tributylammonium) pyrophosphate in dry DMF (1.5 mL) and tri-n-butylamine (0.3 mL) was added to the reaction mixture. The progress of the reaction was monitored by $^{31}$P NMR. Quantitative formation of desired material was observed after 15 minutes by formation of new peaks at around 106 ppm (and disappearance of peaks at 125 ppm). Then N,N-diisopropylethyl-amine-borane complex (1 mL) was added and the reaction mixture stirred for another 5 hours. The completion of the boronation step was confirmed by disappearance of phosphorous signals at 106 ppm and appearance of a broad signal 88–90 ppm. The cyclic product was hydrolyzed with water (30 mL) at room temperature for 3 hours and then the reaction mixture was extracted with dichloromethane (2×60 mL). The aqueous layer was evaporated to dryness to the crude product. The crude product was dissolved in a 0.2 M solution of triethylammonium bicarbonate buffer (pH=7) and purified by reverse phase and ion exchange HPLC (using conditions identical as for other triphosphates) to give the product in 45% yield (Table 5, compound 1).

$^{13}$C NMR (D$_2$O): δ=166.9 (C-4); 152.1 (C-2); 137.74 (C-6); 112.12 (C-5); 85.82+85.73 (C-1'+C-2'); 50.7 (C-3'); 65.7 (C-5'); 38.85 (C-2'); 12.5 (C5-CH$_3$); $^{31}$P NMR (D2O): δ=82–87 (br, 1P, α-P), −8.24 (d, 1P, γ-P), −22.01, 21.30 (dd, 1P, β-P).

Example 8

Procedure for the Synthesis of α-borano-α-thio-triphosphate Nucleosides

Solid support bound cyclic triphosphite nucleoside (4, FIG. 1) was prepared generally as illustrated in Example 2 above. The cyclic triphosphite nucleoside was oxidized with borane-N,N-diisopropylethylamine complex. The reaction mixture was agitated for 180 minutes at 25° C. and excess oxidation reagent was removed by extensive washing with dry acetonitrile (20 mL) and DMF (10 mL). The resulting cyclic triphosphate was treated with a solution of Li$_2$S in dimethyl-formamide in the presence of crown ether (18-crown-6) (8 mL at 25° C. for 120 minutes) to give the solid support bound triphosphate. The solid support was treated with 25% aqueous ammonia in a sealed glass vial (15 hours at 25° C. and 2 hrs at 55° C.). The resulting ammonia solution of α-borano-α-thiotriphosphate nucleoside was evaporated to dryness. The residue was dissolved in a 0.2M solution of triethylammonium bicarbonate buffer (pH=7) and purified by reverse phase and ion exchange HPLC.

Example 9

Procedure for the Synthesis of α-dithiotriphosphate Nucleosides

Solid support bound cyclic triphosphite nucleoside (4, FIG. 1) was prepared generally as illustrated in Example 2 above. The cyclic triphosphite nucleoside was oxidized with a 5% solution of elemental sulfur in carbon disulfide, pyridine and trietylamine (95/95/5, v/v/v) with agitation for 120 minutes at 25° C. The solid support was repeatedly washed with dry acetonitrile (20 mL). The resulting cyclic triphosphate nuclcoside was treated with a 0.2M solution of Li$_2$S and 18-crown-6 ether in dimethyl-formamide (8 mL at 25° C. for 120 minutes). The solid support was treated with 25% aqueous ammonia in a sealed glass vial (15 hours at 25° C. and 2 hrs at 55° C.). The resulting ammonia solution of α-dithiotriphosphate nucleoside was evaporated to dryness. The residue was dissolved in a 0.2M solution of triethylammonium bicarbonate buffer (pH=7) and purified by reverse phase and ion exchange HPLC.

Example 10

Procedure for the Synthesis of α-seleno-α-thiotriphosphate Nucleosides

Solid support bound cyclic triphosphite nucleoside (4, FIG. 1) is prepared generally as illustrated in Example 2 above. The cyclic triphosphite nucleoside was oxidized with a 0.2M solution of 3H-1,2-benzothiaselenol-3-one in acetonitrile and triethylamine (95/5, v/v). The reaction mixture is agitated for 120 minutes at 25° C. The support is washed repeatedly with dry acetonitrile (20 mL). The oxidized cyclic intermediate is treated with a 0.2M solution of Li$_2$S in dimethylformamide (8 mL) in the presence of a crown ether (18-crown-6, 500 mg) at 25° C. for 120 minutes). The support is treated with 25% aqueous ammonia in a sealed glass vial (15 hours at 25° C. and 2 hrs at 55° C.). The resulting ammonia solution of α-seleno-α-thio triphosphate nucleoside is evaporated to dryness. The residue is dissolved in a 0.2M solution of triethylammonium bicarbonate buffer (pH=7) and purified by reverse phase and ion exchange HPLC.

Example 11

Procedure for the Synthesis of α-amino-α-thiotriphosphate Nucleosides

Solid support bound cyclic triphosphite nucleoside (4, FIG. 1) is prepared generally as illustrated in Example 2 above. The cyclic triphosphite nucleoside is oxidized with iodine in the presence of the corresponding amine in an organic solvent. Ammonia is used to attach an amino group and a primary amine having a single substituent defined by $R_1$ in example 3 above is used to attach a substituted amino group at the α-position. Reaction is performed by addition of ammonia (0.5M in dioxane) or a desired primary amine (4 mL) to the solid support suspended in iodine solution in an organic solvent such as tetrahydrofuran (224 mg in 5 mL). Next the reaction mixture is agitated for 40 minutes at 25° C. The solid support is repeatedly washed with dry tetrahydrofuran (10 mL) and dry acetonitrile (10 mL). The solid support is treated with a 0.2M solution of $Li_2S$ in dimethylformamide (8 mL) in the presence of a crown ether (18-crown-6, 500 mg) at 25° C. for 120 minutes. The support is treated with 25% aqueous ammonia in a sealed glass vial (15 hours at 25° C. and 2 hrs at 55° C.). The resulting ammonia solution of α-alkylamino-α-thio triphosphate nucleoside is evaporated to dryness. The residue is dissolved in a 0.2M solution of triethylammonium bicarbonate buffer (pH=7) and purified by reverse phase and ion exchange HPLC.

Example 12

Procedure for the Synthesis of α-Substituted-γ-Amino Triphosphate Nucleosides The oxidized cyclic intermediate (as in Structure 5 of FIG. 2) of Examples 3 and 4 are treated with ammonia or a primary amine (—$NHR_1$) to give the corresponding γ-substituted-α-modified support bound triphosphate nucleoside.

α-Borano-γ-(N-propyl)amino triphosphate nucleoside

Solid support bound cyclic triphosphite nucleoside (4, FIG. 1) is prepared as illustrated in Example 2 above. The oxidation of the cyclic triphosphite nucleoside is carried out using borane-N,N-diisopropylethylamine complex. The reaction mixture is agitated for 180 minutes at 25° C. and the oxidation reagent is removed by repeated washing with dry acetonitrile (20 mL) and DMF (10 mL). The oxidized intermediate is treated with N-propylamine to prepare the γ-amino derivative.

The α-borano-γ-(N-propyl)amino triphosphate is cleaved and deprotected by treating the solid support with 25% aqueous ammonia in a sealed glass vial (15 hours at 25° C. and 2 hours at 55° C.). The cooled ammonia solution of crude α-amino modified nucleoside triphosphate is evaporated to dryness. The residue is dissolved in a 0.2M solution of triethylammonium bicarbonate buffer (pH=7) and purified by reverse phase and ion exchange HPLC to give the α-borano-γ-(N-propyl)amino triphosphate (6, FIG. 2).

Example 13

Assay for the Inhibition of HCV NS5B

This assay can be used to measure the ability of the nucleoside triphosphates of the present invention to inhibit the enzymatic activity of the RNA-dependent RNA polymerase (NS5B) of the hepatitis C virus (HCV) on a heteromeric RNA template.

The following describes assay buffer conditions: (50 μl-total/reaction)

20 mM Tris, pH 7.5
50 μM EDTA
5 mM DTT
2 mM $MgCl_2$
80 mM KCl
0.4 U/μl RNAsin (Promega, stock is 40 units/μl)
0.75 μg t500 (a 500 nt RNA made using T7 runoff transcription with a sequence from the NS2/3 region of the hepatitis C genome)
1.6 μg purified hepatitis C NS5B (form with 21 amino acids C-terminally truncated)
1 μM A, C, U, GTP (nucleoside triphosphate mix)
[alpha-$^{32}$P]-GTP or [alpha-$^{32}$P]-ATP The compounds were tested at various concentrations up to 100 μM final concentration.

An appropriate volume of reaction buffer was made including enzyme and template t500. Nucleoside derivatives of the present invention were pipetted into the wells of a 96-well plate. A mixture of nucleoside triphosphates (NTP's), including the radiolabeled GTP, was made and pipetted into the wells of a 96-well plate. The reaction was initiated by addition of the enzyme-template reaction solution and allowed to proceed at room temperature for 1–2 hours.

The reaction was quenched by addition of 20 μl 0.5 M EDTA, pH 8.0. Blank reactions in which the quench solution is added to the NTPs prior to the addition of the reaction buffer were included.

50 μL of the quenched reaction was spotted onto DE81 filter disks (Whatman) and allowed to dry for 30 minutes. The filters were washed with 0.3 M ammonium formate, pH 8 (150 mL/wash until the cpm in 1 mL wash is less than 100, usually 6 washes). The filters were counted in 5-mL scintillation fluid in a scintillation counter.

The percentage of inhibition is calculated according to the following equation: %Inhibition={1–(cpm in test reaction–cpm in blank)/(cpm in control reaction–cpm in blank)}×100.

Representative compounds tested in the HCV NS5B polymerase assay exhibited $IC_{50}$'s less than 100 micromolar.

Inhibition data is tabulated below.

TABLE 2

Percent Inhibition (% I) of HCV NS5B RNA polymerase

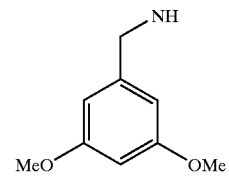

| Bx[a] | $X_1$ | $Y_3$ | $Y_2$ | % I (ATP) | % I (GTP) |
|---|---|---|---|---|---|
| 1 G | OH | OH | SH (Rp) | 82.3 | 73.4 |
| 2 G | $OCH_3$ | OH | SH (Rp) | 89.4 | 88.2 |
| 3 G | $OCH_3$ | $NH_2$ | SH (Rp) | 22.9 | 22.7 |
| 4 C | $OCH_3$ | $NH_2$ | SH (Sp) | −14.1 | −12.7 |
| 5 T | H | $NH_2$ | $BH_3$ (Rp) | −0.83 | 1.94 |
| 6 T | H | OH | $BH_3$ (Sp) | 5.57 | 10.5 |
| 7 G | $OCH_3$ | OH | SH (Sp) | 12.9 | 13.5 |
| 8 G | $OCH_3$ | $NH_2$ | SH (Rp) | 7.64 | 8.24 |
| 9 C | $OCH_3$ | $NH_2$ | SH (Rp) | −14.8 | −16.3 |
| 10 T | H | OH | $BH_3$ (Sp) | 5.42 | 6.88 |
| 11 T | H | $NH_2$ | $BH_3$ (Rp) | 1.88 | 7.87 |
| 12 T | H | OH | NH(n-butyl) | 5 | −1.13 |
| 13 G | $OCH_3$ | OH | $NH(CH_3)$ | 67.3 | 68.7 |
| 14 G | $OCH_3$ | OH | NH(n-propyl) | 76.3 | 80.3 |
| 15 G | OH | OH | $BH_3$ (Sp) | 45 | 99 |
| 16 G | OH | OH | $BH_3$ (Rp) | 26 | 35 |
| 17 T | H | OH | $NH_2$ | 0.1 | −6 |
| 18 G | $OCH_2CH_2OCH_3$ | OH | $NH(OCH_2CH_2CH_2OCH_3)$ | 7.6 | −5 |
| 19 G | $OCH_3$ | OH | $NH(OCH_2CH_2CH_2OCH_3)$ | 93 | 93.3 |
| 20 G | $OCH_3$ | OH | $NH_2$ (Rp/Sp mix) | 81 | 79.3 |
| 21 G | $OCH_3$ | OH | $BH_3$ (Sp) | 97.5 | 99.7 |
| 22 G | $OCH_3$ | OH | $BH_3$ (Rp) | 100 | 99.7 |
| 23 G | $OCH_3$ | OH | NH(n-butyl) | 90 | 91 |
| 24 G | $OCH_3$ | OH | NH(cyclopentyl) | 56 | 59 |
| 25 G | $OCH_3$ | OH | NH(benzyl) | 89 | 93 |
| 26 G | $OCH_3$ | OH | 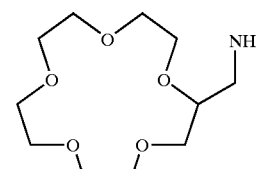 | 94 | 92 |
| 27 G | $OCH_3$ | OH | 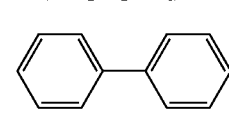 | 88 | 86 |
| 28 G | $OCH_3$ | OH | $NH(OCH_2CH_2SCH_3)$ | 94 | 93 |
| 29 G | $OCH_3$ | OH | $NH(OCH_2CH_2CH_2SCH_3)$ | 94 | 93 |
| 30 G | $OCH_3$ | OH | $NH(OCH_2CH_2OCH_3)$ | 93 | 94 |
| 31 G | $OCH_3$ | OH | 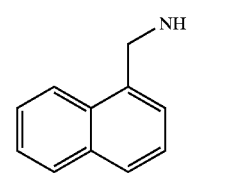 | 76 | 77 |
| 32 G | $OCH_3$ | OH | $NH(OCH_2CH_2OCH_2CH_3)$ | 70 | 73 |
| 33 G | $OCH_3$ | OH | NH(allyl) | 74 | 77 |
| 34 G | $OCH_3$ | OH |  | 92 | 93 |

TABLE 2-continued

Percent Inhibition (% I) of HCV NS5B RNA polymerase

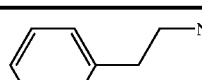

| Bx[a] | X₁ | Y₃ | Y₂ | % I (ATP) | % I (GTP) |
|---|---|---|---|---|---|
| 35 G | OCH₃ | OH | (2-pyridyl-ethyl)-NH | 83 | 84 |
| 36 G | OCH₃ | OH | (N-methyl-pyrrolidinyl-ethyl)-NH | 83 | 84 |
| 37 G | OCH₃ | OH | (imidazolyl-propyl)-NH | 68 | 69 |
| 38 G | OCH₃ | NH₂ | SeH (Sp) | 45 | 35 |
| 39 G | OCH₃ | OH | SeH (Rp) | 92 | 93 |
| 40 G | OCH₃ | NH₂ | SeH (Rp) | 57 | 53 |
| 41 G | OCH₃ | OH | SeH (Sp) | 45 | 38 |
| 42 A | OCH₃ | OH | BH₃ (Sp) | 86 | 81 |
| 43 A | OCH₃ | OH | BH₃ (Rp) | 56 | 48 |

[a]G = guanine, A = adenine, C = cytosine, T = thymine.

Example 14

Assay for the Inhibition of HCV RNA Replication

The compounds of the present invention can be evaluated for their ability to affect the replication of Hepatitis C Virus RNA in cultured hepatoma (HuH-7) cells containing a subgenomic HCV Replicon. The details of a suitable assay are described below. This Replicon assay is a modification of that described in Lohmann, et al., *Science*, 1999, 285, 110, which is incorporated herein by reference in its entirety.

The assay is an in situ Ribonuclease protection, Scintillation Proximity based-plate assay (SPA). 80,000 cells are plated in 200 µl of media containing 0.8 mg/ml G418 in 96-well cytostar plates (Amersham). Compounds are added to cells at various concentrations up to 100 µM in 1% DMSO and cultured for 24 hrs. Cells are fixed (20 min, 10% formalin), permeabilized (20 min, 0.25% Triton) and hybridized (overnight, 50° C.) with a single-stranded $^{33}$P RNA probe complementary to the (+) strand NS5B (or other genes) contained in the RNA viral genome. Cells are washed, treated with RNAse, washed, heated to 65° C. and counted in a Top-Count. Inhibition of replication is read as a decrease in count per minute (cpm).

Human HuH-7 hepatoma cells, which are selected to contain a subgemomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Example 15

Assay for the Inhibition of Human DNA Polymerase Alpha and Beta (Counter Screen)

The ability of the nucleoside derivatives of the present invention to inhibit human DNA polymerases can be measured in the following assay.

Reaction conditions: 50 µL reaction volume.
Reaction buffer components:
20 mM Tris-HCl, pH 7.5
200 µg/mL bovine serum albumin
100 mM KCl
2 mM β-mercaptoethanol
10 mM MgCl₂
1.6 µM dA, dG, dC, dTTP
α-$^{33}$P-dATP
Enzyme and template:
0.05 mg/mL gapped fish sperm DNA template
0.01 U/µL DNA polymerase α or β
Preparation of gapped fish sperm DNA template:
Add 5 µL 1 M MgCl₂ to 500 µL activated fish sperm DNA (USB 70076);
Warm to 37° C. and add 30 µL 65 U/µL exonuclease III (GibcoFRL 18013-011);
Incubate 5 min at 37° C.;
Terminate reaction by heating to 65° C. for 10 min;
Load 50–100 µL aliquots onto Bio-spin 6 chromatography columns (Bio-Rad 732-6002) equilibrated with 20 mM Tris-HCl, pH 7.5;
Elute by centrifugation at 1,000× g for 4 min;
Pool eluate and measure absorbance at 260 nm to determine concentration.

The DNA template is diluted into an appropriate volume of 20 mM Tris-HCl, pH 7.5 and the enzyme is diluted into an appropriate volume of 20 mM Tris-HCl, containing 2 mM β-mercaptoethanol, and 100 mM KCl. Template and enzyme are pipetted into microcentrifuge tubes or a 96-well plate. Blank reactions excluding enzyme and control reactions excluding test compound are also prepared using enzyme dilution buffer and test compound solvent, respectively. The reaction is initiated with reaction buffer with components as listed above. The reaction is incubated for 1 hour at 37° C. The reaction is quenched by the addition of 20 μL of 0.5M EDTA. 50 μL of the quenched reaction is spotted onto Whatman DE81 filter disks and air dried. The filter disks are repeatedly washed with 150 mL 0.3M ammonium formate, pH 8 until 1 mL of wash is <100 cpm. The disks are washed twice with 150 mL absolute ethanol and once with 150 mL anhydrous ether, dried and counted in 5 mL scintillation fluid.

The percentage of inhibition is calculated according to the following equation: % inhibition={1−(cpm in test reaction−cpm in blank)/(cpm in control reaction−cpm in blank)}×100.

Example 16

HIV Infectivity Assay

The ability of nucleoside derivatives of the present invention to inhibit HIV infectivity and HIV spread can be measured using the following assays.

Infectivity Assay: Assays are performed with a variant of HeLa Magi cells expressing both CXCR4 and CCR5 selected for low background β-galactosidase (β-gal) expression. Cells are infected for 48 hours, and β-gal production from the integrated HIV-1 LTR promoter is quantified with a chemiluminescent substrate (Galactolight Plus, Tropix, Bedford, Mass.). Inhibitors are titrated (in duplicate) in twofold serial dilutions starting at 100 mM; percent inhibition at each concentration is calculated in relation to the control infection.

Inhibition of HIV spread: The ability of the compounds of the present invention to inhibit the spread of the human immunodeficiency virus (HIV) can be measured by the method described in U.S. Pat. No. 5,413,999, and Vacca, et al., *Proc. Natl. Acad. Sci. USA*, 1994, 91, 4096, each of which is incorporated herein by reference in its entirety.

Example 17

Cytotoxicity Assay

The nucleoside derivatives of the present invention can also be screened for cytotoxicity against cultured hepatoma (HuH-7) cells containing a subgenomic HCV Replicon in an MTS cell-based assay as described in the assay below. The HuH-7 cell line is described in Nakabayashi, et al., *Cancer Res.*, 1982, 42, 3858, which is incorporated herein by reference in its entirety.

Cell cultures are prepared in appropriate media at concentrations of approximately $1.5 \times 10^5$ cells/mL for suspension cultures in 3 day incubations and $5.0 \times 10^4$ cells/mL for adherent cultures in 3 day incubations. 99 μL of cell culture is transferred to wells of a 96-well tissue culture treated plate, and 1 μL of 100-times final concentration of the test compound in DMSO was added. The plates are incubated at 37° C. and 5% $CO_2$ for a specified period of time. After the incubation period, 20 μL of CellTiter 96 Aqueous One Solution Cell Proliferation Assay reagent (MTS) (Promega) is added to each well and the plates are incubated at 37° C. and 5% $CO_2$ for an additional period of time up to 3 hours. The plates are agitated to mix well and absorbance at 490 nm is read using a plate reader. A standard curve of suspension culture cells is prepared with known cell numbers just prior to the addition of MTS reagent. Metabolically active cells reduce MTS to formazan. Formazan absorbs at 490 nm. The absorbance at 490 nm in the presence of compound is compared to absorbance in cells without any compound added. See, e.g., Cory, et al., *Cancer Commun.*, 1991, 3, 207, which is incorporated herein by reference in its entirety.

Example 18

Pharmaceutical Formulation

The following is an example of an oral composition including a compound of the present invention. 50 mg of a compound of the present invention is formulated with sufficient finely divided lactose to provide a total amount of about 580 to about 590 mg to fill a size 0 hard gelatin capsule.

Example 19

Inhibition of HIV-RT Activity

Compounds of the present invention were tested for their ability to inhibit HIV-reverse transcriptase (HIV-RT) activity using the below described assay. Results are provided below in Table 4.

The objective of the assay is to select agents which specifically inhibit the activity of the HIV Reverse Transcriptase by measuring transcription/incorporation with a heteromeric RNA template annealed to a DNA primer.

Assay Buffer Conditions:

50 mM Tris, pH 7.8;

1 mM DTT;

6 mM $MgCl_2$, 80 mM KCl;

0.2% polyethylene glycol 8000;

100 nM t500 template (a 500-nt RNA made using T7 runoff transcription with a sequence from the NS2/3 region of the hepatitis c genome);

200 nM pD500 (DNA primer 5'-TTGAAATGACTGCGGTACGGC-3');

5 nM wild-type HIV RT (dilution buffer: 50 mM Tris, 7.8; 80 mM KCl; 1 mM DTT; 0.2% PEG 8K); and 5 μM dATP, TTP, dCTP, dGTP+[alpha-$^{33}$P]-dATP.

Compounds were tested at 0.5, 5, and 50 μM final concentration, and control compound L-738372 was tested at 0.5, 5, and 50 nM (DMSO).

pD500 (200 nM) was annealed to t500 (100 nM) by heating for 3 minutes at 65° C. The mixture was allowed to cool to room temperature (about 1 hour). Compounds or carrier were pipetted into the wells of a 96-well plate (PEG-coated). An appropriate volume of reaction buffer was prepared including the enzyme and the primer/template. The enzyme/template mixture was added to the compound. The dNTP mixture, including the labeled dATP, was added to initiate the reaction. Only the control compound (L-738372) was pre-incubated at room temperature with the enzyme/template mix for 30 minutes before addition of the dNTPs. There was no pre-incubation with template and enzymes for the compounds of interest.

The reaction was allowed to continue for 1 hour at room temperature. Then, 20 μL 0.5 M EDTA, pH 8.0, was added to quench and mix the reaction.

50 μL of the quenched reaction was spotted onto DE81 filter disks (Whatman). The disks were allowed to dry for 30 min and washed with 0.3 M ammonium formate, pH 8 (150 mL/wash until the cpm in 1 mL wash is less than 100, usually 6 washes). 5 mL scintillation fluid was used to count. (In an alternative procedure, 50 μL of the quenched reaction can be spotted onto DE81 filter plates. The plates can be washed twice with 250 μL of 2× PBS; washed once with 250 μL water; washed once with 50 μL ethanol, and allowed to dry for a few minutes. 50 μL scintillation fluid can be added to count.)

Percent inhibition was calculated according to the following equation:

% inhibition=100×{1−(*cpm* in test reaction−*cpm* in blank)/(*cpm* in control reaction−*cpm* in blank)}.

TABLE 4
Inhibition of HIV-RT
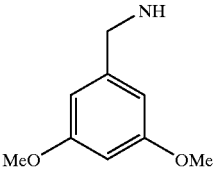
| | Bx | X₁ | Y₃ | Y₂ | % I (100 μM) | % I (10 μM) |
|---|---|---|---|---|---|---|
| 1 | G | OCH₃ | OH | SH | 17.14 | −1.14 |
| 2 | G | OH | OH | unmodified | 91.43 | 57.29 |
| 3 | G | OH | OH | BH₃ | 50.57 | 2.47 |
| 4 | G | OH | OH | BH₃ | −9.15 | −8.61 |
| 5 | G | OCH₂CH₂OCH₃ | OH | NH(CH₂)₃OCH₃ | −24.91 | −11.17 |
| 6 | G | OCH₃ | OH | NH(CH₂)₃OCH₃ | −12.38 | −7.28 |
| 7 | G | OCH₃ | OH | BH₃ (Sp) | 57.59 | 17.23 |
| 8 | G | OCH₃ | OH | BH₃ (Rp) | −36.08 | −11.06 |
| 9 | G | OCH₃ | OH | NH(n-butyl) | −22.36 | −12.43 |
| 10 | G | OCH₃ | OH | 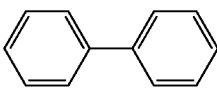 | −11.9 | −6.41 |
| 11 | G | OCH₃ | OH | (4'-aminomethyl-benzo-15-crown-5) | −17.25 | 5.37 |
| 12 | G | OCH₃ | OH | NH(CH₂CH₂SCH₃) | −3.2 | 5.5 |
| 13 | G | OCH₃ | OH | NH(CH₂CH₂OCH₃) | −17.89 | −14.01 |
| 14 | G | OCH₃ | OH | biphenyl-CH₂NH | −12.93 | −2.25 |

Example 20

Inhibition of HIV-RT Activity

AZT analogs were tested for their ability to inhibit HIV-reverse transcriptase (HIV-RT) activity according to the assay described in Example 19. Results are provided below in Table 5.

TABLE 5

Inhibition of HIV-RT

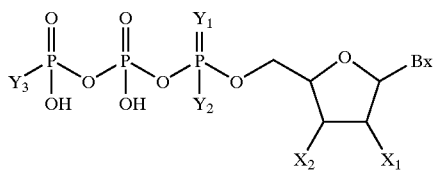

| | $Bx^a$ | $X_2$ | $X_1$ | $Y_2$ | % Control Activity[b] (100 μM) | % Control Activity[b] (10 μM) |
|---|---|---|---|---|---|---|
| 1 | T | $N_3$ | H | OH | 10 | 7 |
| 2 | T | $N_3$ | H | $BH_3$ (Rp) | 8 | 9 |
| 3 | T | $N_3$ | H | $BH_3$ (Sp) | 8 | 11 |
| 4 | T | OH | H | $BH_3$ | 64 | 70 |

[a] T = thymine.
[b] % Inhibition = 100 − (% Control Activity).

As those skilled in the art will appreciate, numerous changes and modifications can be made to the preferred embodiments of the invention without departing from the spirit of the invention. It is intended that all such variations fall within the scope of the invention.

The entire disclosure of each publication cited herein is hereby incorporated by reference.

What is claimed is:

1. A compound of formula I

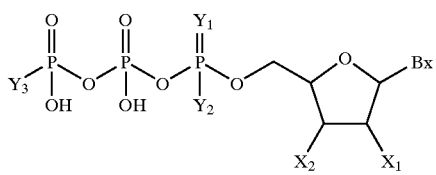

I wherein:

$Y_1$ is S and $Y_2$ is $NHR_1$; or $Y_1$ is Se and $Y_2$ is SH;

$Y_3$ is $NHR_1$, OH, $C_1$–$C_{12}$ alkyl, or $C_1$–$C_{12}$ O-alkyl;

$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;

Bx is an optionally protected heterocyclic base moiety;

one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;

J is a bifunctional linking moiety, selected from the group consisting of hydroxyl, acyl, amino, alkoxy, carboxy, benzyl, phenyl, nitro, thiol, thioalkoxy, halogen, alkyl, aryl, alkenyl and alkynyl; and SM is a solid support medium.

2. The compound of claim 1 wherein $Y_1$ is S and $Y_2$ is $BH_3$.

3. The compound of claim 1 wherein $Y_3$ is OH.

4. The compound of claim 1 wherein Bx is adenine, guanine, thymine, cytosine, or uracil.

5. A compound of formula I:

I wherein:

$Y_1$ is O and $Y_2$ is $BH_3$; or $Y_1$ is Se and $Y_2$ is OH;

$Y_3$ is $NHR_1$, $C_1$–$C_{12}$ alkyl, or $C_1$–$C_{12}$ O-alkyl;

$R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;

Bx is an optionally protected heterocyclic base moiety;

one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;

J is a bifunctional linking moiety; selected from the group consisting of hydroxyl, acyl, amino, alkoxy, carboxy, benzyl, phenyl, nitro, thiol, thioalkoxy, halogen,alkyl, aryl, alkenyl and alkynyl; and SM is a solid support medium.

6. A compound of formula I:

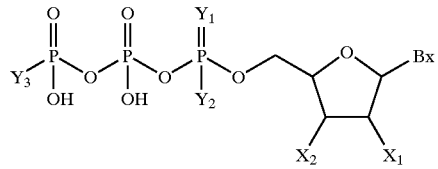

I wherein:
$Y_1$ is Se and $Y_2$ is OH;
$Y_3$ is $NHR_1$, OH, $C_1$–$C_{12}$ alkyl, or $C_1$–$C_{12}$ O-alkyl;
  $R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl substituted or unsubstituted $C_5$–$C_{20}$ alkylaryl substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto;
Bx is an optionally protected heterocyclic base moiety;
one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;
  J is a bifunctional linking moiety; and
  SM is a solid support medium.

7. The compound of claim 6 wherein $Y_3$ is OH.

8. A compound of formula I:

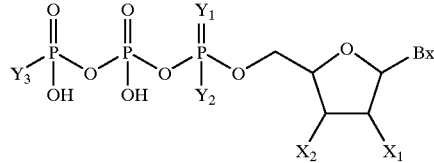

I wherein:
$Y_1$ is O and $Y_2$ is $BH_3$; or
$Y_1$ is Se and $Y_2$ is OH;
$Y_3$ is $NHR_1$;
  $R_1$ is hydrogen substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl substituted or unsubstituted $C_5$–$C_{20}$ alkylaryl, substituted or unsubstituted $C_5$–$C_{20}$ heterocycloalkyl, substituted or unsubstituted $C_5$–$C_{20}$ alkylaryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_1$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_1$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto:
Bx is an optionally protected heterocyclic base moiety;
one of $X_1$ and $X_2$ is H, hydroxyl, a protected hydroxyl, or a sugar substituent group and the other of $X_1$ and $X_2$ is hydroxyl, a protected hydroxyl, azido, or -O-J-SM;
  J is a bifunctional linking moiety; selected from the group consisting of hydroxyl, acyl, amino, alkoxy, carboxy, benzyl, phenyl, nitro, thiol, thioalkoxy, halogen, alkyl, aryl, alkenyl and alkynyl; and
SM is a solid support medium.

9. A compound of formula VIII:

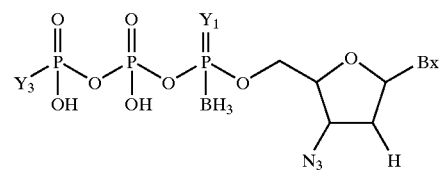

VIII wherein:
$Y_1$ is O or S;
$Y_3$ is $NHR_1$ OH, $C_1$–$C_{12}$ alkyl, or $C_1$–$C_{12}$ O-alkyl;
  $R_1$ is hydrogen, substituted or unsubstituted $C_1$–$C_{12}$ alkyl, substituted or unsubstituted $C_2$–$C_{12}$ alkenyl, substituted or unsubstituted $C_2$–$C_{12}$ alkynyl, substituted or unsubstituted $C_5$–$C_{20}$ aralkyl, substituted or unsubstituted $C_5$–$C_{20}$ alkylaryl, substituted or unsubstituted $C_5$–$C_{20}$ heterocycloalkyl, substituted or unsubstituted $C_5$–$C_{20}$ aryl, substituted or unsubstituted $C_5$–$C_{20}$ heteroaryl, said substituted moieties comprising one or more substituents selected from hydrogen, halo, $C_1$–$C_{12}$ alkyl, $C_2$–$C_{12}$ alkenyl, $C_2$–$C_{12}$ alkynyl, $C_5$–$C_{20}$ aryl, $C_1$–$C_{12}$ alkoxy, alkoxyalkyl, O-alkylaminoalkyl, O-alkylimidazolyl, S-alkyl, amino, alkylamino, dialkylamino, arylamino, diarylamino, $C_5$–$C_{20}$ aryl, $C_5$–$C_{20}$ heteroaryl, $C_1$–$C_{12}$ cycloalkyl, $C_1$–$C_{12}$ heterocyclolalkyl, O-aryl, S-aryl, O-aralkyl, S-aralkyl, NH-aralkyl, nitro, cyano, aldehyde, carboxylic acid, hydroxy, alkylcarbonyl, aminocarbonyl, or mercapto; and
Bx is adenine, thymine, cytosine, guanine, or uracil.

10. The compound of claim 9 wherein Bx is thymine.

11. The compound of claim 9 wherein $Y_1$ is O.

12. A pharmaceutical formulation comprising a compound of claim 1 and a pharmaceutically acceptable excipient.

13. A pharmaceutically formulation comprising a compound of claim 5 and a pharmaceutically acceptable excipient.

14. A pharmaceutical formulation comprising a compound of claim 9 and a pharmaceutically acceptable excipient.

* * * * *

UNITED STATES PATENT AND TRADEMARK OFFICE
CERTIFICATE OF CORRECTION

PATENT NO. : 6,900,308 B2  
APPLICATION NO. : 10/195980  
DATED : May 31, 2005  
INVENTOR(S) : Tadeusz Wyrzykiewicz et al.

It is certified that error appears in the above-identified patent and that said Letters Patent is hereby corrected as shown below:

1) Title Page:
Item [56], References Cited, OTHER PUBLICATIONS, "Brownlee" reference, please delete "$m_7$" and insert therefor --$m^7$--;

2) Title Page:
Item [56], References Cited, OTHER PUBLICATIONS, "Tomasz" reference, please delete "5'pyrophosphate" and insert therefor --5'-pyrophosphate--;

3) Title Page:
Item [56], References Cited, OTHER PUBLICATIONS, "Tomasz" reference, please delete "3'-5-'" and insert therefor --3'-5'--;

4) Column 35, Claim 6, line 21, please insert --,-- between "aralkyl" and "substituted";

5) Column 35, Claim 6, line 22, please insert --,-- between "alkylaryl" and "substituted";

6) Column 35, Claim 6, line 41, please insert --selected from the group consisting of hydroxyl, acyl, amino, alkoxy, carboxy, benzyl, phenyl, nitro, thiol, thioalkoxy, halogen, alkyl, aryl, alkenyl and alkynyl;-- between ";" and "and";

7) Column 35, Claim 8, line 59, please insert --,-- between "hydrogen" and "substituted";

8) Column 35, Claim 8, line 65, please delete "alkylaryl" and insert therefor --aryl--;

9) Column 36, Claim 8, line 2, please delete "$C_1$-$C_{12}$ alkynyl" and insert therefor --$C_2$-$C_{12}$ alkynyl--;

10) Column 36, Claim 8, line 6, please delete "$C_1$-$C_1$" and insert therefor --$C_1$-$C_{12}$--;

11) Column 36, Claim 9, line 34, please insert --,-- between "$NHR_1$" and "OH";

UNITED STATES PATENT AND TRADEMARK OFFICE
CERTIFICATE OF CORRECTION

PATENT NO. : 6,900,308 B2
APPLICATION NO. : 10/195980
DATED : May 31, 2005
INVENTOR(S) : Tadeusz Wyrzykiewicz et al.

It is certified that error appears in the above-identified patent and that said Letters Patent is hereby corrected as shown below:

12) Column 36, Claim 13, line 60, please delete "pharmaceutically" and insert therefor --pharmaceutical--.

Signed and Sealed this

Seventeenth Day of June, 2008

JON W. DUDAS
*Director of the United States Patent and Trademark Office*